(12) United States Patent
Issenmann et al.

(10) Patent No.: US 8,221,489 B2
(45) Date of Patent: Jul. 17, 2012

(54) DEVICE AND METHOD FOR TREATING A BODY LUMEN

(75) Inventors: Gonzague L. Issenmann, Clichy (FR); Hikmat Hojeibane, Princeton, NJ (US)

(73) Assignee: Stentys, Paris (FR)

( * ) Notice: Subject to any disclaimer, the term of this patent is extended or adjusted under 35 U.S.C. 154(b) by 115 days.

(21) Appl. No.: 12/544,591

(22) Filed: Aug. 20, 2009

(65) Prior Publication Data
US 2011/0046717 A1 Feb. 24, 2011

(51) Int. Cl.
*A61F 2/06* (2006.01)
(52) U.S. Cl. ..................................... 623/1.15
(58) Field of Classification Search .............. 606/108, 606/194, 200; 623/1.1–1.12, 1.15–1.17, 623/1.2
See application file for complete search history.

(56) References Cited

U.S. PATENT DOCUMENTS

| | | | |
|---|---|---|---|
| 6,042,606 A | 3/2000 | Frantzen | |
| 6,241,746 B1 | 6/2001 | Bosma et al. | |
| 6,267,777 B1 | 7/2001 | Bosma et al. | |
| 6,325,825 B1 | 12/2001 | Kula et al. | |
| 6,468,302 B2 | 10/2002 | Cox et al. | |
| 6,669,723 B2 | 12/2003 | Killion et al. | |
| 6,682,554 B2 | 1/2004 | Oepen et al. | |
| 6,706,061 B1 | 3/2004 | Fischell et al. | |
| 6,755,856 B2 | 6/2004 | Fierens et al. | |
| 6,852,124 B2 | 2/2005 | Cox et al. | |
| 6,878,162 B2 | 4/2005 | Bales et al. | |
| 7,029,492 B1 | 4/2006 | Mitsudou et al. | |
| 7,232,453 B2 | 6/2007 | Shimon | |
| 7,540,930 B2 | 6/2009 | Moriuchi et al. | |
| 2004/0024444 A1* | 2/2004 | Moore | 623/1.15 |
| 2005/0004655 A2 | 1/2005 | Von Oepen et al. | |
| 2007/0005103 A1 | 1/2007 | Schaeffer | |
| 2007/0055365 A1 | 3/2007 | Greenberg et al. | |
| 2007/0093744 A1 | 4/2007 | Elmaleh | |
| 2007/0135891 A1 | 6/2007 | Schneider | |
| 2007/0244118 A1* | 10/2007 | Kubo et al. | 514/235.5 |
| 2008/0051876 A1 | 2/2008 | Ta et al. | |
| 2008/0086190 A1* | 4/2008 | Ta | 623/1.11 |
| 2008/0215135 A1 | 9/2008 | Seguin et al. | |
| 2008/0221664 A1 | 9/2008 | Bales et al. | |
| 2008/0262598 A1 | 10/2008 | Elmaleh | |
| 2009/0254172 A1* | 10/2009 | Grewe | 623/1.15 |

(Continued)

FOREIGN PATENT DOCUMENTS

DE 10 2007 019 772 A1 10/2008
(Continued)

OTHER PUBLICATIONS

Oct. 26, 2010 International Search Report issued in PCT/IB2010/053327.

(Continued)

*Primary Examiner* — Ryan Severson
*Assistant Examiner* — Ashley Cronin
(74) *Attorney, Agent, or Firm* — Oliff & Berridge, PLC

(57) ABSTRACT

A device and method for treating a body conduit/lumen having an undesired reduced diameter include delivering an expandable stent in a contracted configuration to a target location. The stent has small cells that form an open tight mesh providing the effective capture of small particles such as thrombi. Preferably, the tight mesh is combined with structure that permits creation of large side openings to accommodate lumen branches.

38 Claims, 7 Drawing Sheets

FOREIGN PATENT DOCUMENTS

| | | |
|---|---|---|
| FR | 2 911 063 A1 | 7/2008 |
| WO | WO 99/39661 A2 | 8/1999 |
| WO | WO 00/28922 A1 | 5/2000 |
| WO | WO 00/53122 A1 | 9/2000 |
| WO | WO 03/055414 A1 | 7/2003 |
| WO | WO 2008/030291 A1 | 3/2008 |

OTHER PUBLICATIONS

U.S. Appl. No. 12/247,077, filed Oct. 7, 2008, in the name of Seguin et al.

Mortier at al., "Comparison of drug-eluting stent cell size using micro-CT: important data for bifurcation stent selection," *EuroIntervention*, 2008, vol. 4, pp. 391-396.

\* cited by examiner

| | # OF STRUTS | # OF CELLS | # OF BRIDGES | STRUT LENGTH | STRUT WIDTH | CELL AREA | CONNECTED STATE CIRCLE DIAMETER | DISCONNECTED STATE CIRCLE DIAMETER | CIRCLE RATIO (DISCONNECTED STATE CIRCLE DIAMETER/ CONNECTED STATE CIRCLE DIAMETER) |
|---|---|---|---|---|---|---|---|---|---|
| | MIN/MAX | MIN/MAX | MIN/MAX | MIN/MAX | MIN/MAX | MIN/MAX | MIN/MAX | | |
| | | | | mm | mm | mm$^2$ | mm | mm | |
| EXAMPLES OF EMBODIMENTS | 24/84 | 6/24 | 6/24 | 0.239/1.2 | 0.030/0.83 | 0.18/1.754 | 0.1/0.615 | 3.647 | 6/25 |
| VISION (3.0) | | | | 1.334 | 0.91 | 1.1271 | 0.903 | | |
| LIBERTÉ (3.0) | | | | 0.95 | 0.88 | 0.5339 | 0.682 | | |

FIG. 5

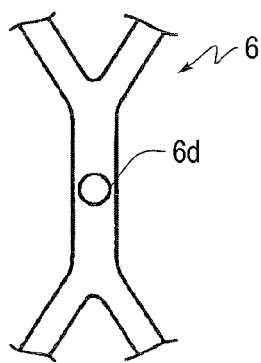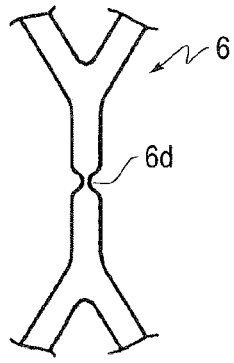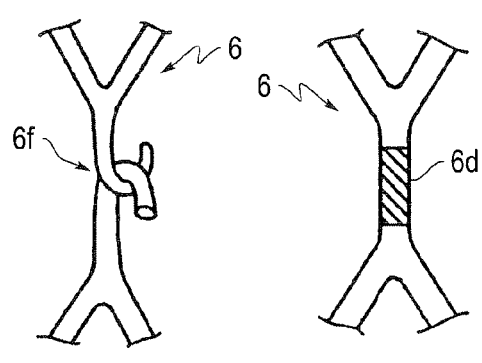
FIG. 10  FIG. 11  FIG. 12  FIG. 13
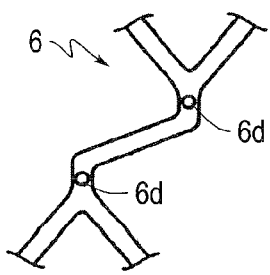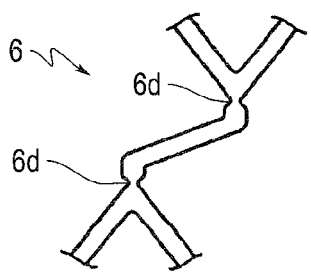
FIG. 14  FIG. 15

DEVICE AND METHOD FOR TREATING A BODY LUMEN

FIELD OF THE INVENTION

The present invention relates to a device and method for treating a body conduit/lumen, such as a blood vessel, in an animal such as a human. In embodiments, the treatment is directed to a conduit that has an undesired reduced diameter (e.g., an area of stenosis in a blood vessel). Examples of such conduits that may be treated by the method of the present invention include, for example, blood vessels that have an undesired reduced diameter, such as may result from an obstruction within the blood vessel and/or a spasm of the blood vessel such as may occur in connection with acute myocardial infarction, but are not limited to such conduits.

BACKGROUND

Acute myocardial infarctions are the result of partial or complete blockage of one or more coronary arteries, in which the blockage causes an undesired reduced diameter in the bodily vessel. Percutaneous treatment of acute myocardial infarctions may include the delivery and placement of a stent at the site of the blockage. Treating bodily conduits that have an undesired reduced diameter by means of a radially expandable tubular implant with a cutout or open meshed structure, currently called a "stent," is known. This device may be introduced in an unexpanded/contracted state into the conduit to be treated and delivered to the area of the conduit that has an undesired reduced diameter. The device is then radially expanded, particularly by means of an inflatable balloon, or, when it has a self-expandable structure, the stent may be released from a sheath that contains the stent in its contracted state. With self-expanding stents in particular, the self-expansion of the stent further ensures that there is continuous radial force anchoring the stent in place.

Various stents are available to treat bodily lumens having an undesired reduced diameter, including balloon-expandable stents and self-expanding stents. These stents typically have a weaved open mesh that forms the outer wall of the stent.

Although a stent may be used to treat an undesired reduced diameter of a bodily conduit, the open mesh structure of the stent, when formed of a plurality of cells defining small openings, may reduce the stent's utility for bifurcation stenting. For example, a stent with a cell size that defines a small opening may obstruct access to a side branch. However, the use of a stent with cells having larger openings may reduce the structural integrity of the stent. Further, many stents lack the ability to capture and prevent thrombi from traveling through the patient's vascular system due to the cutout and open meshed structure of the stents. See "Comparison of Drug-Eluting Stent Cell Size Using Micro-CT: Important Data for Bifurcation Stent Selection," EuroIntervention, 2008; vol. 4, pp 391-396.

In addition, a stent itself may cause problems over time, such as causing thrombosis formation (e.g., clots) within a blood vessel. For example, during bifurcation stenting with a stent having small cell openings, struts that are not in contact with the vessel wall may cause thrombosis formation.

The inability to capture and prevent thrombi from traveling through the patient's vascular system is particularly relevant with drug eluting stents, e.g., stents that elute anti-restenotic drugs from a polymer coating. The polymer coating on these stents may be responsible for late stent thrombosis when the stent is not well apposed to the vessel wall. Although such issues could be reduced by bioresorbable stents, the effective treatment of body lumens that have an undesired reduced diameter remains difficult because of an inability to capture and prevent passage of particles such as blood clots/thrombi after placement of the stent.

Abbott Laboratories' Vision stent has an open mesh outer wall that includes cells having an area of approximately 1.1271 mm$^2$ and a relatively large opening when the stent is expanded to a 3.0 mm diameter (the diameter of a nominal blood vessel in which the stent may be used). Cells with such openings may be too large for effectively capturing smaller thrombi, while simultaneously blocking side branches more than is desirable.

Other known stents that have smaller cell sizes suffer even more from the inability to allow adequate blood flow to side branches because of the small cell size. For example, Boston Scientifics' Liberté stent has an open mesh outer wall that includes cells having an area of 0.5339 mm$^2$ when the stent is expanded to a 3.0 mm diameter and smaller openings than the Vision stent that may not be capable of providing desirable levels of side branch access while still not providing desired thrombus protection.

Accordingly there remains a demand for devices and methods for effectively treating bodily conduits, particularly branched conduits, that have an undesired reduced diameter.

SUMMARY

In embodiments of the present invention, an expandable implant in a contracted configuration is delivered to a target location of a bodily lumen to be treated. The target location is, for example, a location of an undesired reduced diameter of the bodily lumen. The stent has a first cross-sectional area in a contracted state that is smaller than cross-sectional areas of the stent in expanded states. The expandable stent includes a plurality of circular portions, and a plurality of bridges connecting the circular portions together. The circular portions may be formed having various configurations/arrangements, such as a plurality of struts that connect in an end-to-end relationship at junctions in a zigzag arrangement. The bridges connect consecutive circular portions to each other along a longitudinal direction of the stent. The bridges may connect the adjacent circular portions at every junction, every other junction, or may connect at any combination of junctions or separate from junctions. In addition, one or more bridges may be disconnectable/breakable.

In embodiments of the present invention, the length and arrangement of the bridges and circular portions create an open tight mesh having a plurality of cells. Each of the plurality of cells is configured to have a small opening as defined below. The tight mesh and the structure of the stent permit creation of large side openings to accommodate lumen branches.

Embodiments of stents of the invention have a tight mesh configuration in expanded states, which enables the stents to capture both large and small thrombi and thus prevent or reduce the likelihood of thrombi/blood clots, including those that form after implantation of the stent, traveling through the patient's vascular system. Accordingly, the tight mesh configurations in embodiments of the present invention provide optimum treatment for acute myocardial infarctions by capturing thrombi/blood clots. Thus the need for anti-thrombotic medication, for example in the form of prolonged anti-platelet therapy, may be reduced or avoided in embodiments.

Embodiments include self-expanding stents. For example, the stent may be allowed to initially self-expand to an expanded lumen diameter, preferably after contractile spasms and/or blood clots in the lumen are treated, reduced or eliminated, upon the stent's release from a delivery sheath.

Other embodiments may radially expand to an expanded lumen diameter in response to an external force. For example, an inflatable balloon may be utilized by being extended within the stent along or parallel to a longitudinal axis of the stent through the stent and inflated within the stent. The inflation of the balloon thereby exerts an outward force to expand the stent to an expanded lumen diameter.

In embodiments, portions of the stent are configured to be disconnectable in situ to allow sidebranch access anywhere along the length of the stent and/or the circumference of the stent, with little or no obstruction of sidebranch access.

Embodiments may be, but need not be, bioresorbable or drug-eluting. They may be, or may not be, used in connection with angioplasty.

Methods according to the invention may be utilized for treating various bodily conduits/lumens such as blood vessels, including un-branched lumens and branched lumens such as vascular bifurcations.

Other examples of self-expanding stents and their respective methodologies that may be utilized in embodiments are described in prior pending U.S. Patent Applications Ser. Nos. 11/884,114 and 12/247,077, the disclosures of which are hereby incorporated by reference in their entirety, and the following discussion and drawings, but the invention is not limited to such disclosures. The disclosure of the '114 application includes embodiments that permit opening of a side wall of a stent to one or more side branches of a lumen. The disclosure of the '077 application includes embodiments that permit a stent to expand over time such that the stent migrates inside, through and then outside of the treated bodily lumen. In addition, the disclosure of the '114 application includes structures configured for treating Y-shaped bifurcations in which the present invention may be useful, while the disclosure of the '077 application discusses embodiments that may be may be used in various bodily conduits/lumens. These and other features of the cited applications are incorporated by reference herein.

As discussed above, embodiments of the present invention may be used in un-branched lumens, Y-shaped bifurcation, or in lumens with one or more side branches. For acute treatments or the like, the branches may be ignored, the diameters of the branches may be underestimated, and/or the branches may be considered insignificant during initial stent placement. Accordingly, in embodiments, access to the side branch(es) may be provided during the stent placement procedure, or optionally in subsequent treatments.

BRIEF DESCRIPTION OF THE DRAWINGS

FIG. 5 is a table including examples of embodiments of the present invention in comparison with known stents;

FIGS. 10-15 depict various embodiments of disconnectable bridges.

DETAILED DESCRIPTION OF EMBODIMENTS

Figure 1:
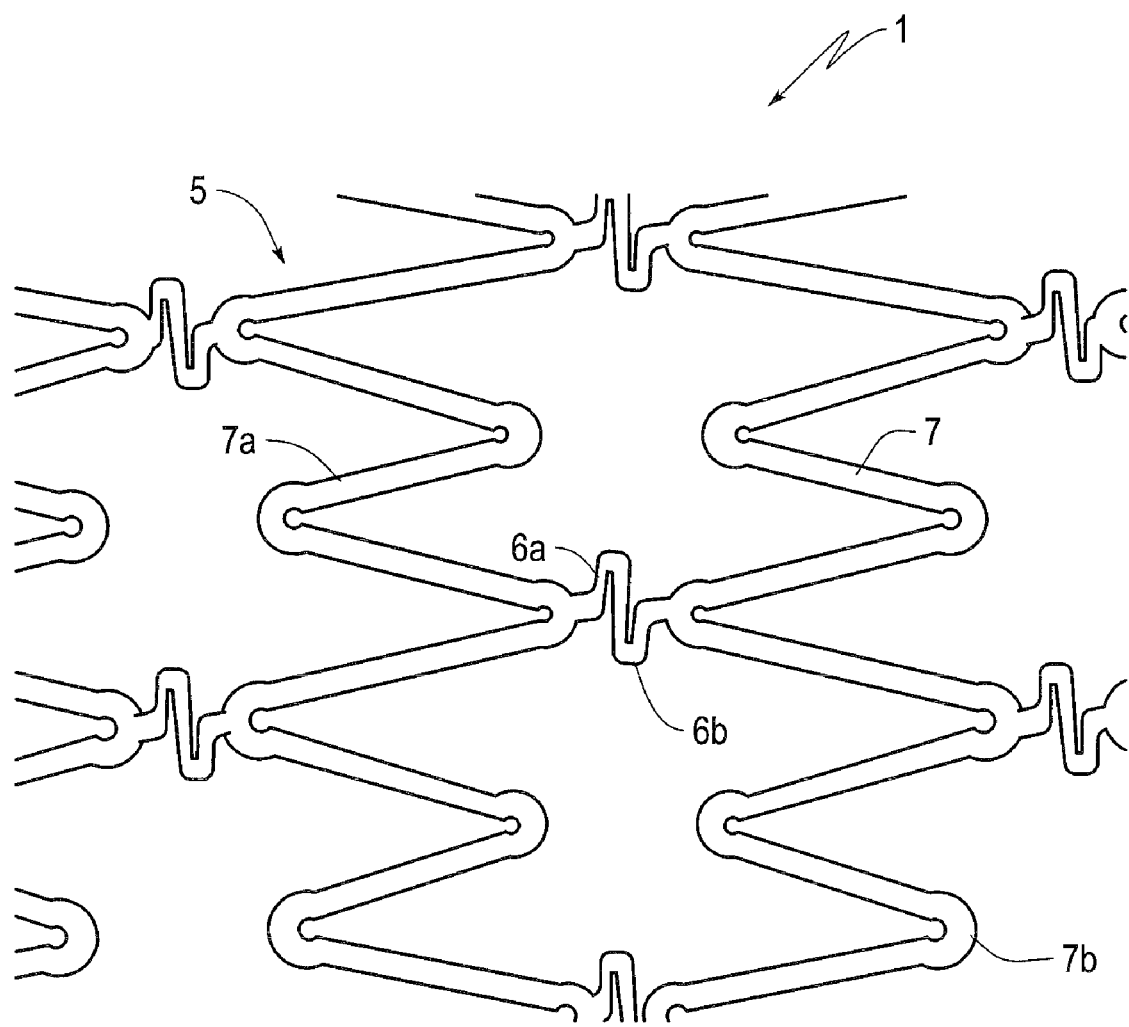
FIG. 1 is a side view of a portion of a stent in an expanded condition.

FIG. 1 is a side view of a portion of a radially expandable tubular implant 1, called a "stent." The stent 1 comprises a plurality of circular (annular) portions 5 and a plurality of bridges 6 connecting the circular portions 5 to each other. In embodiments, the bridges 6 may be breakable during or after deployment. In embodiments, each circular portion 5 is formed by a zigzag portion 7 (e.g., structure that may have a substantially flat, polygonal (e.g., rectangular or trapezoidal), round, oval or other cross-sectional shape formed, for example from wire or from a tube that has been cut-out such as by laser cutting) formed of struts 7a that are connected to each other at junctions 7b in an end-to-end relationship. Struts 7a preferably, but not necessarily, have substantially identical lengths. Other arrangements of circular sections and bridges, such as curving structures, may also be suitable in embodiments.

The circular portions 5 are formed such that the stent 1 may pass from a radially contracted state to a radially expanded state by a change of configuration, for example, at the junctions 7b of the zigzag portion 7. The radially contracted state allows engagement of the stent 1 in a sheath or on a balloon that is used to route/deliver the stent 1 to the area of a bodily conduit that has an undesired reduced diameter, where the radially expanded state allows the stent 1 to give the bodily conduit the desired diameter (e.g., the natural diameter).

For example, in a radially contracted state such as a stent may have in a delivery catheter, an exemplary stent diameter may be from 1.0 to 2.0 mm, such as 1.2 to 1.6 mm. In an unbranched target conduit, the diameter may expand, for example, to 2.0 to 4.5 mm, such as 2.75 to 4.0 mm or 3 mm. In a branched target conduit, one longitudinal portion of the stent is often more expanded than the other. Thus, for example, one portion could be expanded to a diameter corresponding to that of an unbranched conduit, while another portion may be expanded in the area of a carina to 2.0 to 3.5 mm or more, such as 2.25 to 3.25 mm or 2.5 to 3.0 mm. Fully expanded without the constraint of the target conduit, the same stent might have a diameter such as 3.0 to 9.0 mm, such as 3.0 to 7.5 mm or 4.0 to 7.5 mm. Of course, these ranges are merely exemplary and other ranges are also contemplated.

The stent 1 may, for example, be self-expandable or balloon-expandable. For example, the stent 1 may expand from its radially contracted state to its radially expanded state when it is released from a sheath. The sheath may be retracted to allow the stent to self-expand. Alternatively, expansion may take place only upon application of radially outward force by inflation of a balloon within the stent. The stent may, for example, be formed of a shape-memory metal such as a nickel-titanium alloy known as "nitinol." The stent may be formed of other materials, including, for example, various other metals (as used herein, "metals" includes elemental metals and metal-containing alloys).

In embodiments, treatment may be directed to un-branched conduits, or directed to conduits with one or more branches.

In embodiments, which may include acute treatments or the like, such as treatment of a myocardial infarction, branches may be ignored during initial stent placement, and side access may be provided in subsequent treatments that are one to twenty-four hours, one to seven days, one to four weeks, one to twelve months, or even years later, or access to the side branch(es) and optional stenting thereof may be provided during the stent placement procedure.

The expandable stent 1 is delivered in a contracted configuration to a target location that may be the location of a lumen having an undesired diameter. An expanded configuration of the stent allows the bodily conduit to return to its natural diameter. In embodiments, when in a fully self-expanded configuration, the stent 1 may have a diameter that is slightly or much larger than a target diameter(s) over an entire length of the stent 1. The stent 1 may be configured to exert a substantially constant radially outward force against the bodily conduit over substantially a full range of expansion of the stent 1. The target diameter may be substantially constant along the length of the target location, or may change over the length of the target location. Thus, for example in an unbranched target location, the target diameter may be relatively uniform. As another example, in a branched target location, the target diameter may change substantially at the area of branching. The fully-expanded diameter of the stent in either instance may be uniform or change over the length of the stent.

Figure 2:
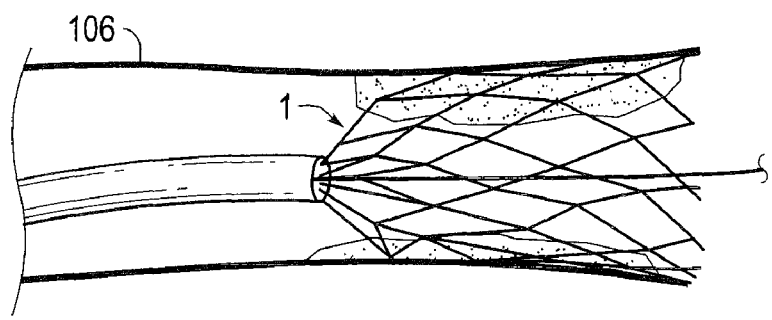
FIGS. 2-4 are schematic views of successive steps of positioning a stent in an un-branched conduit.
Figure 3:
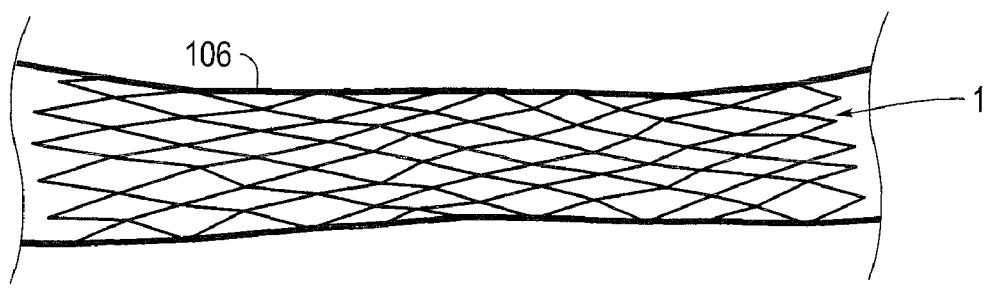
Figure 4:
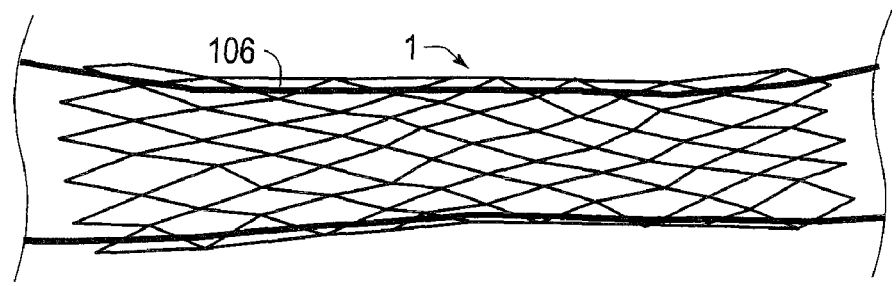

For example, FIG. 2 schematically depicts the deployment of a self-expandable stent 1 in a partially occluded un-branched conduit 106. FIG. 3 schematically depicts the stent in an expanded state, in which the lumen of the un-branched conduit 106 has substantially regained its natural diameter, as a result of the self-expansion of the stent 1. FIG. 4 depicts the stent 1 after gradual migration of the stent 1 through the walls of the un-branched conduit 106.

The body conduit to be treated may be a blood vessel. In embodiments, the target location may be a site of an undesired reduced diameter of the flow passage through the blood vessel, such as a site of a thrombus located in the blood vessel, which may result in acute myocardial infarction. In embodiments, the target location may be a site of a contractile spasm of the blood vessel, and/or a site of trauma to the blood vessel.

The target diameter of the lumen to be treated is often difficult to determine. Thus, the determination of the target diameter may be based on various factors and considerations. For example, the target diameter may be based on readily observable patient morphology (e.g., sex, age, weight and the like). In such a determination, the target diameter may have a very imprecise correlation to the natural diameter of the target location in the body conduit. The target diameter may also or alternatively, for example, be based on a feature with a more precise correlation to the natural diameter of the target location, such as a diameter of the body conduit at a location upstream of the target location, and/or on a diameter of a parallel branch(es) that is included in a branching system with the body lumen, such as a coronary tree.

In embodiments, an obstruction of the body conduit at the target location, such as a thrombus, or atheroma plaques, that may occur in connection with acute myocardial infarction may be treated before the stent 1 is delivered to the target location. In embodiments, the treatment of the obstruction may include supplying a thrombolytic agent or an anti-spastic agent to the target location prior to the delivery of the stent 1 to the target location.

In embodiments, the treatment of the obstruction may include mechanical treatment. For example, the treatment of the obstruction may include deoccluding the obstruction with a percutaneous de-occluding tool, debulking the obstruction with a de-bulking tool, and/or performing balloon angioplasty at the site of the obstruction.

In addition, the obstruction may be treated prior to the delivery of the stent 1 by aspiration of a thrombus, or by laser treatment of the obstruction.

As discussed above, in embodiments, treatment may be directed to un-branched conduits, Y-shaped bifurcations, or to conduits with one or more side branches. Herein, except as otherwise noted, Y-shaped bifurcations and side branches are addressed interchangeably. In embodiments, portions of the stent may be configured to be disconnected in situ to create an access site through a wall of the stent to a side branch.

In embodiments, the stent 1 may include disconnectable (e.g., breakable) bridges 6 that connect adjacent circular portions 5. In the embodiments depicted in FIGS. 1 and 7, breakable bridges 6 comprise three lateral portions 6a and two curved portions 6b for connecting adjacent circular portions 5 at junctions 7b.

The bridges 6 preferably have a certain flexibility that, in conjunction with the flexibility of the circular portions 5, allows the stent 1 to have a certain longitudinal flexibility when it is in a radial expansion state. Because of this longitudinal flexibility, embodiments of this invention may be used in various conduits in a curved state. For example, a part of stent 1 may be positioned in the main conduit of a bifurcation while the other part of the stent 1 is positioned in one of secondary conduits of the bifurcation even when the main conduit and the secondary conduit form an angle with each other.

The bridges 6 may or may not be disconnectable (e.g., breakable) during deployment of the stent 1. The disconnection of bridges 6 allows the stent 1 to be largely or completely open in such a way as to form two tubular stent parts that are fully or partially separated.

The circular portions 5 of the stent 1 may include twenty-four or fewer to eighty-four or more struts 7a, such as twenty-four to forty-eight struts. In embodiments, the struts 7a may have, for example, a length of 0.2 mm-1.5 mm, preferably 0.239 mm-1.2 mm, more preferably 0.25 mm-1.15 mm, and a width of 0.025 mm-0.9 mm, preferably 0.03 mm-0.83 mm, more preferably 0.04 mm-0.79 mm.

Figure 7:
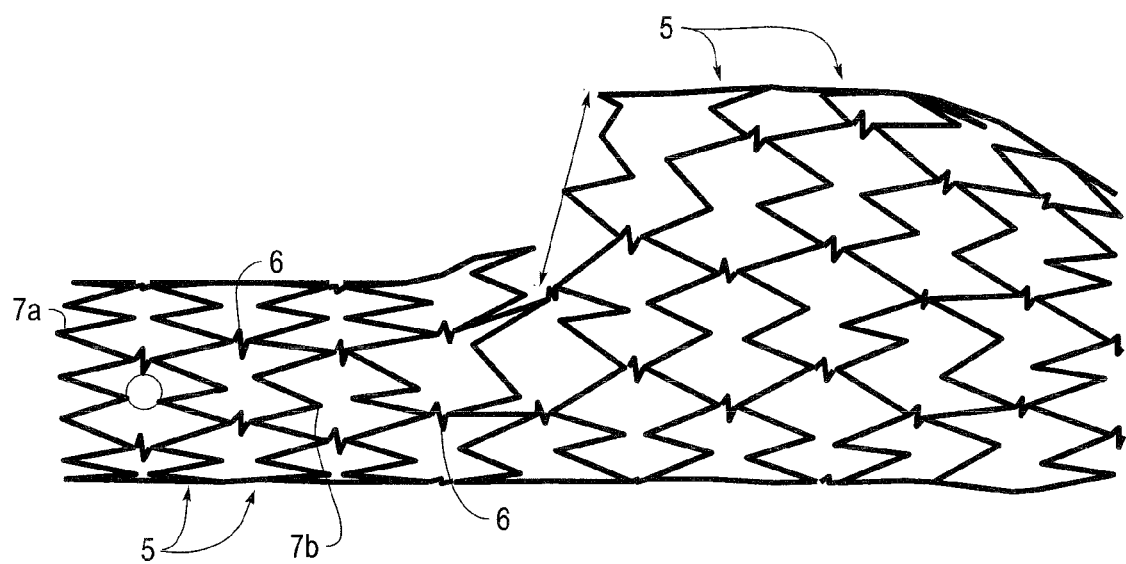
FIG. 7 is a view of a portion of the stent of FIG. 6, after disconnecting one or more bridges of the stent, or of a stent with a reduced number of bridges.

The stent 1 may include five or fewer up to twenty-eight or more bridges 6, preferably six to twenty-four bridges 6. See FIG. 5 for examples of appropriate structures. A relatively higher number of bridges can be appropriate for embodiments with disconnectable bridges than for embodiments without disconnectable bridges, in order to facilitate providing larger openings at side branches upon differential expansion of different portions of a stent, for example at a bifurcation of a conduit. Thus, for example, preferred embodiments with disconnectable bridges may have six to sixteen bridges, while preferred embodiments without disconnectable bridges may have two to nine bridges. FIG. 7 depicts such differences graphically in a stent that is constrained in a smaller diameter conduit at the left-hand side, but in a larger diameter conduit at the right-hand side (such as at a bifurcation of the conduit). FIG. 7 depicts an embodiment with disconnectable bridges after disconnection of one or more bridges, and it simultaneously depicts an embodiment without disconnectable bridges, but having fewer bridges to start with.

Figure 6:
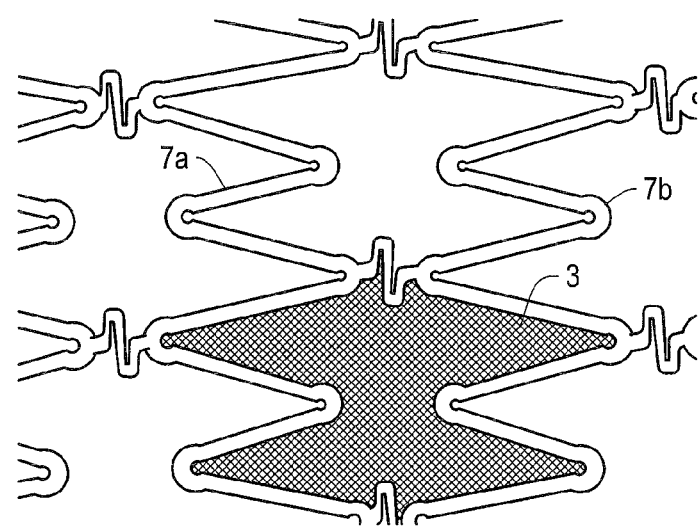
FIG. 6 is a side view of a portion of a stent in an expanded condition, before disconnecting bridges of the stent.

The arrangement of circular portions 5 and bridges 6 creates an open tight mesh having a plurality of cells 3 (see, e.g., FIG. 6). The stent 1 may include, for example, five to twenty eight or more cells 3, preferably six to twenty-four, more preferably six to sixteen cells 3. Each of the plurality of cells 3 may have, for example, a wide range of cell areas while the stent is radially expanded and in a connected state (i.e., while the bridges are not disconnected). For example, the cell area may be from 0.05 to 2.0 mm$^2$, preferably 0.15 to 1.5 mm$^2$, more preferably 0.18 to 1.0 mm². However, regardless of their areas, the cells 3 are configured to provide an open tight mesh arrangement with the ability to capture thrombi/blood clots that may be formed after placement and expansion of the stent in vivo.

Figure 8:
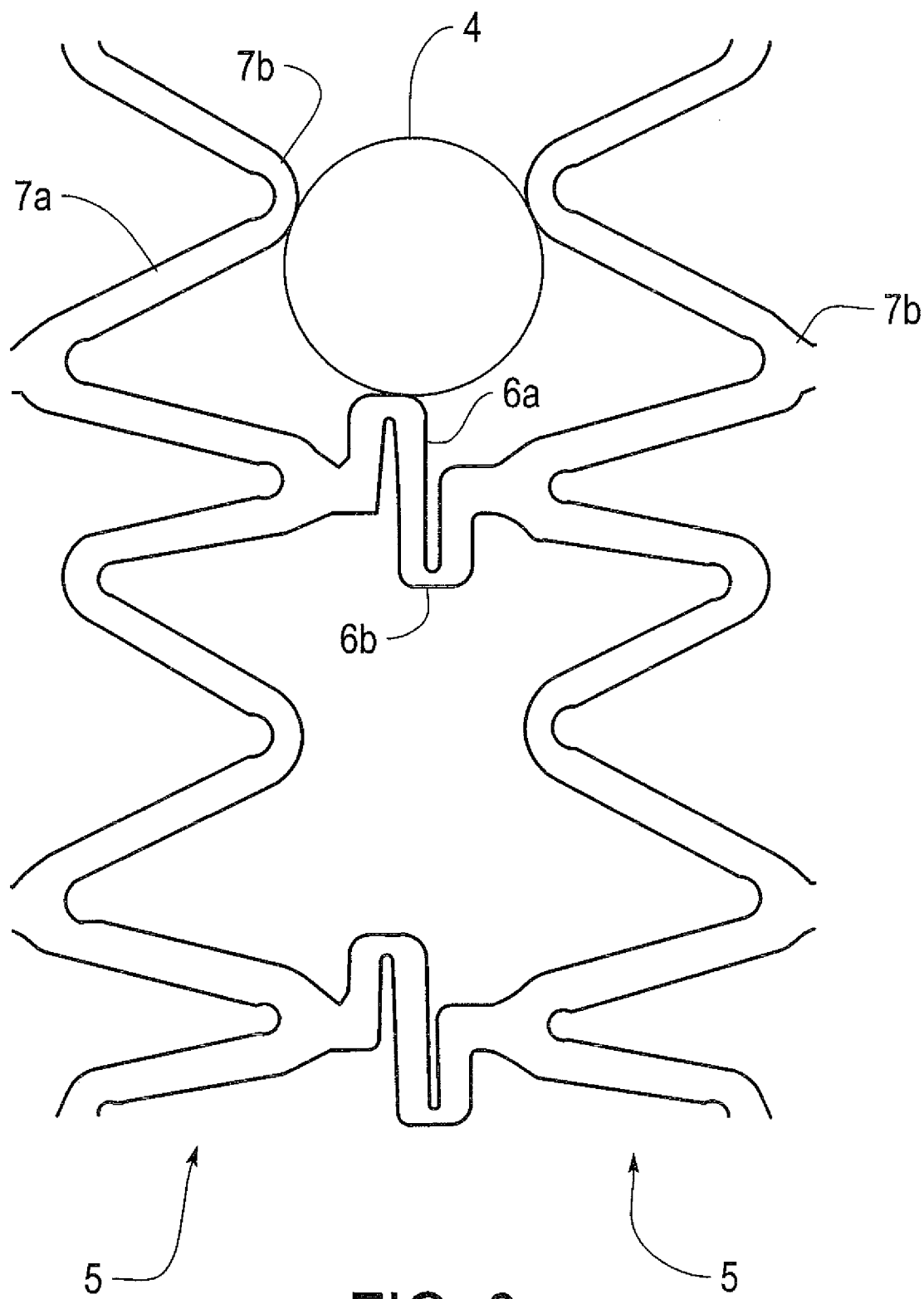
FIG. 8 is a developed view of a portion of a stent in an expanded condition, before disconnecting bridges of the stent.

As depicted in the plane of the developed view of FIG. 8, some or all of the cells 3 are configured such that the largest circle 4 that is capable of fitting within the developed view perimeter of the cell (hereafter "that will fit within a cell") when the stent is expanded to a nominal target diameter of 3.0 mm have a diameter of up to 0.65 mm, preferably 0.05 mm-0.63 mm, more preferably 0.1 mm-0.615 mm, such as 0.3 to 0.4 mm.

The small diameter of the circle 4 enables the stent 1 to capture thrombi and thus prevent thrombi/blood clots, including those that form after implantation of the stent 1, from traveling through the patient's vascular system.

Cells having a long perimeter may be used to facilitate bifurcation stenting by, for example, providing a large side opening anywhere along the length of the stent 1 and/or the circumference of the stent 1 to accommodate enhanced flow and/or additional stent placement relative to a branch. At the same time, the small diameter circle dimension advantageously captures thrombi along the sides of the stent. In embodiments, the length of the perimeter of one or more cells 3 (or enlarged cells resulting from disconnection of one or more bridges) is at least as large as the perimeter of the lumen of a side branch to be treated. The configuration of the cells 3 permits access to a branch lumen whereby in some circumstances an additional stent or stents may be positioned in the branch lumen, allowing adequate vascular wall coverage by the struts 7a, with minimal obstruction of the lumens.

In embodiments, the disconnectable bridges 6 permit the creation of larger side openings to accommodate lumen branches. For example, bridges 6 that connect adjacent circular portions 5 can be broken or otherwise disconnected to create an expanded opening that accommodates a circle, for example, having a diameter of 1-4 mm or more, such as 2-4 mm or 2.5-3.5 mm.

Accordingly, as depicted in FIG. 7, when one or more of the bridges 6 is disconnected, or in the case of a long-perimeter cell (e.g., a smaller number of bridges) without disconnection of any bridges, an access site in the wall of the stent 1 may be created to provide access to a side branch, thereby allowing the stent 1 to have an expanded opening with a sufficiently large diameter to allow much less obstructed or unobstructed flow through the side branch, without compromising the structural integrity of the stent 1. For example, a ratio between the diameter of a circle that fits within the expanded opening formed either by disconnection of one or more bridges or by the configuration of the cells (e.g., the double headed arrow in FIG. 7) and the previously mentioned circle diameter of a cell constrained in a 3 mm diameter conduit lumen is in a range of 5 or 10 to 25.

Figure 9A:
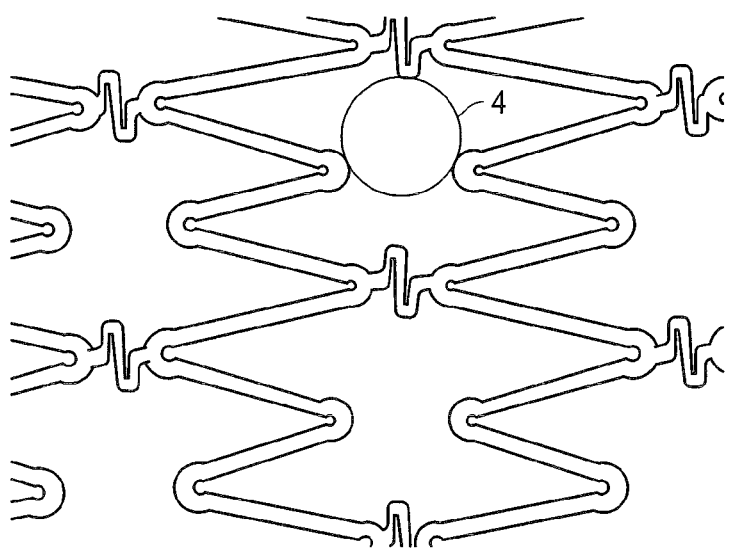
FIG. 9A is a developed view of a portion of a stent of the present invention.
Figure 9B:
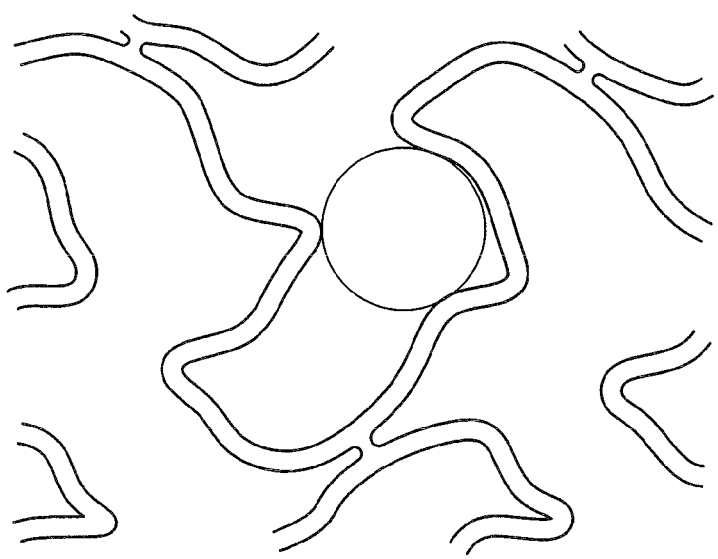
FIGS. 9B and 9C are developed views of known stents.
Figure 9C:
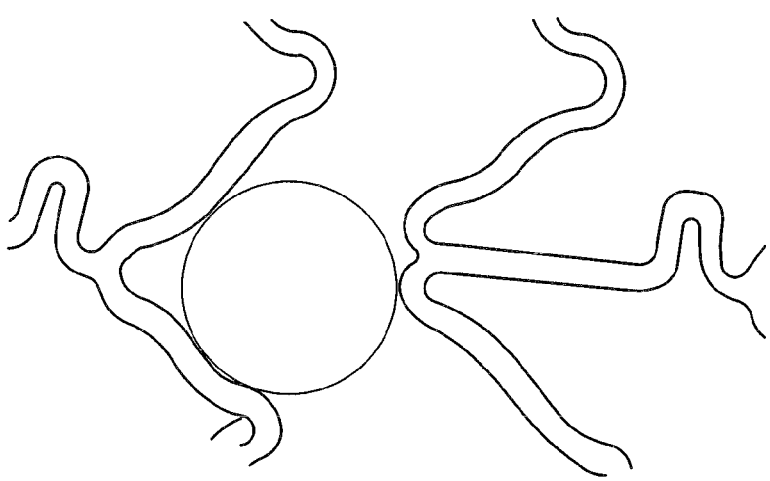

In addition, because of the open tight mesh created by cells 3, the number of struts 7a that are not in contact with a vascular wall is minimized, thereby reducing the formation of thrombi. However, in the event thrombi are formed, the stent 1 is capable of both capturing thrombi and providing access to a side branch. Stents with cells that are capable of fitting circles that have a diameter larger than the circles in embodiments of the present invention may not be as effective in capturing thrombi. For example, Abbott Laboratories' Vision stent (which has cells that are capable of fitting circles with a diameter of at least 0.903 mm when expanded to a 3.0 mm nominal target diameter) and Boston Scientifics' Liberté stent (which has cells that are capable of fitting circles with a diameter of at least 0.682 mm when expanded to a 3.0 mm nominal target diameter), would be less effective in capturing small thrombi and clots and simultaneously allowing adequate branch access. As depicted in FIG. 9A-C, the cells 3 of a stent of the invention (FIG. 9A) are advantageously configured to fit circles having smaller diameters to effectively capture thrombi than prior stents (FIGS. 9B and 9C), without compromising access to lumen branches.

Known stents with small cells lack the ability to create an access site to a side branch and provide a large diameter upon expansion of the stent, without compromising the structural integrity of the stent. For example, Boston Scientifics' Liberté stent has an open mesh outer wall that includes cells with areas that are smaller than cell areas in some embodiments of the present invention and larger than cell areas in other embodiments of the present invention. Nevertheless, as can be seen for example in FIGS. 5 and 9A-C, the circle diameter (and thus area) of these cells is larger than the circle areas of the present invention, and thus the cells provide less thrombus protection. In addition, to provide adequate access to a side branch, it may be necessary to severely distort the cells of the Liberté stent, which may weaken the structural integrity of the Liberté stent. In comparison, in embodiments of the present invention, the cells may be larger and thus may be expanded even further, without compromising the structural integrity or thrombus capturing ability of the stent. Further, in embodiments of the present invention, disconnecting one or two or a few bridges will allow a desired opening to expand to a much larger diameter. For example, as depicted in FIG. 5, in embodiments of the present invention, the diameter of circle 4 may, for example, increase from 0.615 mm to a diameter of 3.647 mm for the circle that fits in the enlarged opening formed when the stent is in a disconnected state at an enlarged area of the conduit (e.g., at a bifurcation), which advantageously provides relatively unobstructed side branch access.

The small circle diameter of the cells 3 may also permit more cells to be included in the stent 1 than in other stents, particularly in the disconnectable embodiments, allowing the stent 1 to retain structural durability even when one or more cells 3 are merged by the disconnection of one or more bridges 6. For example, as depicted in FIG. 7, the stent 1 with the tight mesh structure created by the cells 3, when one or more bridges 6 are disconnected, is capable of expanding to large diameters for effective side branch access without compromising structural integrity of the stent 1.

In practice, in the treatment of a vessel having a reduced diameter, for example, a vessel that that has atheroma plaques along the inner walls of the conduit, a guiding wire may be introduced percutaneously through the conduit to be treated.

A catheter may then be advanced over the wire into the conduit. The catheter contains the stent 1 that is maintained in a state of radial contraction such as by an exterior sliding sheath. When the distal extremity of the catheter is inside the conduit such that the stent is positioned at a target location, the sheath may be slid in such a way so as to release the stent 1, which is deployed in the conduit at the target location. The sliding of the sheath may be a retraction of sheath away from the distal extremity of the catheter. The deployment of the stent 1 allows the atheroma plaques to be compressed such that the conduit regains its adequate and desired diameter (e.g., substantially the natural diameter).

In an example of a balloon expandable embodiment, a stent 1 on the exterior surface of a balloon may be moved along the guide wire to the target location. The balloon may then be inflated such that the balloon exerts a force to cause the stent to expand to an expanded lumen diameter.

In embodiments the stent 1 may have a significantly larger diameter than the target diameter over the whole length of the stent 1. For example, a stent with a substantially uniform diameter may have a diameter more than 50% larger than the size of the treated conduit.

FIGS. 10-15 depict exemplary embodiments of bridges 6 that may be of various shapes and configurations. For example, bridges 6 may be parallel to the longitudinal direction of the stent (FIGS. 10 to 13) and/or oblique with relation to this longitudinal direction of the stent 1 (FIGS. 14 and 15).

Each bridge 6 may comprise one or more are as 6d that may be of reduced resistance to breaking, for example, in the form of one or more thinnings of the section of the bridge, cuts, circular perforations provided in the bridge (FIGS. 10, 11, 14 and 15), or of a grooved or striated area (FIG. 13).

Each bridge 6 may also or alternatively, for example, comprise one or more areas 6d composed of a material different from the material constituting the rest of the stent, optionally suitable for being broken under the separation action exerted by the balloon 11 (FIG. 13). For example, the balloon 11 may be inserted through a cell opening of the stent wall and inflated to a pressure of 4 to 10 atmospheres to cause the bridge to break. Each bridge 6 may comprise two parts 6f forming interconnected hooks (FIG. 12), specific for being separated under the action of separation means, or forming a microlevers-type system (called "MEMS"), specific for being disconnected with the help of a cryotherapy balloon to cool the microlevers.

As appearing from the aforesaid, embodiments of the invention provide devices and methods for allowing the treatment of bodily conduits, for example branched or un-branched lumens, that have the decided advantage of being able to provide more effective treatment than devices and methods known in the art.

It goes without saying that the invention is not limited to the embodiments described above by way of example but that it extends to all embodiments of the invention. For example, only portions of stent 1 may have a meshed structure; markers may be provided to ensure engagement of a balloon through a selected area, for example in the form of radio-opaque markers; separation devices could be one or more balloons, including cryotherapy balloons, a small expansion tool, like small forceps or pliers, at the distal end of a catheter and actuated from the proximal end with wires extending in the lumen of the said catheter, or other separation devices; the stent can be a drug eluting stent; etc.

What is claimed is:

1. A radially expandable tubular implant for treatment of bodily conduits, the implant comprising:
   a plurality of circular portions, the circular portions being circular when viewed along a longitudinal direction of the implant, and
   a plurality of bridges that, when connected, connect two consecutive circular portions to one another and, when disconnected, do not connect the two consecutive circular portions to one another,
   wherein:
      an arrangement of the circular portions and the bridges creates an open mesh defining a plurality of cells,
      the cells are configured such that the largest circle that will fit within a cell when the implant is expanded to a nominal target diameter of 3.0 mm has a first circle diameter of 0.65 mm or less while the implant is in a connected state, and
      the cells are configured such that, in an unconstrained portion of the implant adjacent a portion of the implant that is constrained to a 3.0 mm diameter, a second circle diameter of 2.25 mm will fit within an expanded cell opening between the constrained portion and the unconstrained portion when none, one or a plurality of the bridges are disconnected, wherein when one or a plurality of the bridges must be disconnected to achieve fit of the second circle diameter in the expanded cell opening, the bridges are configured to be disconnected in vivo.

2. The implant of claim 1, wherein said implant is self-expanding.

3. The implant of claim 1, wherein said implant is configured to exert a substantially constant radially outward force over substantially a full range of expansion of said implant.

4. The implant of claim 1, wherein said first circle diameter is in a range of 0.05 mm-0.615 mm.

5. The implant of claim 1, wherein said first circle diameter is in a range of 0.3 mm-0.4 mm.

6. The implant of claim 1, wherein one or more of the bridges is configured to be disconnectable in vivo but not to disconnect under natural body movements.

7. The implant of claim 6, wherein said one or more disconnectable bridges is breakable by expansion of a balloon within a cell at a pressure of 4 to 10 atmospheres.

8. The implant of claim 7, wherein the cells are configured such that upon disconnection of one bridge of the implant in the unconstrained portion of the implant adjacent the portion of the implant that is constrained to a 3.0 mm diameter, a second circle that has a second circle diameter of 2.25 mm will fit within an opening between the constrained portion and the unconstrained portion.

9. The implant of claim 7, wherein the cells are configured such that upon disconnection of two bridges of the implant in the unconstrained portion of the implant adjacent the portion of the implant that is constrained to the 3.0 mm diameter, a second circle that has the second circle diameter of 2.25 mm will fit within the opening between the constrained portion and the unconstrained portion.

10. The implant of claim 1, wherein all of the bridges are configured to be disconnectable in vivo.

11. The implant of claim 1, wherein the cells are configured such that in the unconstrained portion of the implant adjacent the portion of the implant that is constrained to a 3.0 mm diameter, a second circle that has the second circle diameter of 2.25 mm will fit within a cell opening between the constrained portion and the unconstrained portion while no bridge of the implant is in a disconnected state.

12. The implant of claim 11, wherein a ratio between said second circle diameter and said first circle diameter is in a range of 5 to 25.

13. The implant of claim 1, wherein said circular portions are formed by a zigzag arrangement of a plurality of struts connected together in an end-to-end relationship at junctions.

14. The implant of claim 1, wherein said implant is formed from a laser cut tube.

15. The implant of claim 1, wherein none of the bridges are configured to be disconnectable in vivo.

16. A method for treatment of a body lumen, comprising:
    delivering a stent in a contracted configuration to a target location in said body lumen having at least one lumen diameter;
    causing the stent to expand at the target location;
    wherein:
       the stent comprises a plurality of circular portions, the circular portions being circular when viewed along a longitudinal direction of the stent, and a plurality of bridges that, when connected, connect consecutive circular portions to one another and, when disconnected, do not connect the consecutive circular portions to one another, an arrangement of the circular portions and the bridges creates an open mesh defining a plurality of cells, the cells are configured such that the largest circle that will fit within a cell when the stent is expanded to a nominal target diameter of 3.0 mm has a first circle diameter of 0.65 mm or less while the stent is in a connected state, and in an unconstrained portion of the stent adjacent a portion of the stent that is constrained to a 3.0 mm diameter, a second circle diameter of 2.25 mm will fit within an expanded cell opening between the constrained portion and the unconstrained portion.

17. The method of claim 16, wherein said stent is a self-expanding stent and is caused to expand by withdrawing a restraining sheath.

18. The method of claim 16, wherein said stent is a balloon-expandable stent and is caused to expand by expanding a balloon extending within said stent along or parallel to a longitudinal axis of said stent.

19. The method of claim 16, wherein said first circle diameter is in a range of 0.05 mm-0.615 mm.

20. The method of claim 16, wherein said first circle diameter is in a range of 0.3 mm-0.4 mm.

21. The method of claim 16, further comprising disconnecting at least one said bridge while said stent is at said target location to provide the expanded cell opening in said stent at a side branch of said lumen.

22. The method of claim 21, wherein said disconnecting is achieved by breaking at least one said bridge with a balloon extended through a cell opening.

23. The method of claim 21, wherein said at least one bridge is a plurality of said bridges.

24. The method of claim 21, wherein a ratio between a second circle diameter of a second circle that will fit within said expanded opening and said first circle diameter is in a range of 5 to 25.

25. The method of claim 21, comprising disconnecting said at least one bridge during the same procedure in which said stent is delivered to said target location.

26. The method of claim 16, wherein said stent expands without disconnection of a bridge to provide an expanded cell opening at a side branch of said body lumen.

27. The method of claim 26, wherein a ratio between a second circle diameter of a second circle that will fit within said expanded opening and said first circle diameter is in a range of 5 to 25.

28. The method of claim 16, wherein said circular portions form a zigzag arrangement of a plurality of struts connected together in an end-to-end relationship at junctions.

29. The method of claim 16, further comprising treating an obstruction of said lumen at said target location before delivering said stent to said target location.

30. The method of claim 16, wherein said body lumen is a blood vessel.

31. The method of claim 30, further comprising supplying a thrombolytic or anti-spastic agent to said target location prior to delivering said stent to said target location.

32. The method of claim 30, wherein said method is performed to treat an acute myocardial infarction.

33. The method of claim 16, wherein said target location is a site of an obstruction in a blood vessel.

34. A radially expandable tubular implant for treatment of bodily conduits, the implant comprising:

a plurality of circular portions, the circular portions being circular when viewed along a longitudinal direction of the implant, and a plurality of bridges that, when connected, connect two consecutive circular portions to one another and, when disconnected, do not connect the two consecutive circular portions to one another, wherein:

an arrangement of the circular portions and the bridges creates an open mesh defining a plurality of cells, and the cells are configured such that the largest circle that will fit within a cell when the implant is expanded to a nominal target diameter of 3.0 mm has a first circle diameter less than 0.15 mm while the implant is in a connected state.

35. The implant of claim 34, wherein said first circle diameter is in a range of 0.05 mm-0.10 mm.

36. The implant of claim 34, wherein said first circle diameter is 0.10 mm or less.

37. The implant of claim 34, wherein said first circle diameter is 0.05 mm or less.

38. A radially expandable tubular implant for treatment of bodily conduits, the implant comprising:

a plurality of circular portions, the circular portions being circular when viewed along a longitudinal direction of the implant and formed by a zigzag arrangement of struts, the zigzag arrangement of struts resulting in peaks pointing in a first direction and valleys pointing in a second direction, and a plurality of bridges that, when connected, connect two adjacent circular portions to one another such that the peaks of one circular portion are in longitudinal alignment with the valleys of an adjacent circular portion and, when disconnected, do not connect the two consecutive circular portions to one another, wherein:

an arrangement of the circular portions and the bridges creates an open mesh defining a plurality of cells, and the cells are configured such that the largest circle that will fit within a cell when the implant is expanded to a nominal target diameter of 3.0 mm has a first circle diameter of less than 0.15 mm while the implant is in a connected state.

* * * * *